US006579707B2

(12) United States Patent
Fitzgerald et al.

(10) Patent No.: US 6,579,707 B2
(45) Date of Patent: Jun. 17, 2003

(54) STABILIZATION OF ENZYMES DURING FREEZING

(75) Inventors: Stephen Peter Fitzgerald, Co. Antrim (GB); John Campbell, Co. Antrim (GB); John Victor Lamont, Co. Antrim (GB); Marlene King, Co. Antrim (GB)

(73) Assignee: Randox Laboratories Ltd., Northern Ireland (GB)

( * ) Notice: Subject to any disclaimer, the term of this patent is extended or adjusted under 35 U.S.C. 154(b) by 0 days.

(21) Appl. No.: 09/949,757

(22) Filed: Sep. 12, 2001

(65) Prior Publication Data

US 2002/0058319 A1 May 16, 2002

(30) Foreign Application Priority Data

Sep. 20, 2000 (GB) .............................................. 0023057

(51) Int. Cl.[7] .............................. C12N 9/96; C12N 9/04; C12N 9/08; A61K 38/54; A61K 38/44
(52) U.S. Cl. ........................ 435/188; 435/190; 435/192; 435/183; 424/94.3; 424/94.4
(58) Field of Search ................................. 435/188, 190, 435/192, 183; 424/94.3, 94.4

(56) References Cited

U.S. PATENT DOCUMENTS

| 4,465,770 A | | 8/1984 | Modrovich |
| 4,734,360 A | * | 3/1988 | Phillips |
| 4,806,478 A | * | 2/1989 | Stahl |
| 4,812,398 A | * | 3/1989 | Kondo et al. |
| 5,219,751 A | | 6/1993 | Starnes et al. |
| 5,612,468 A | | 3/1997 | Hawkins et al. |
| 5,910,422 A | | 6/1999 | Modrovich et al. |
| 6,071,706 A | | 6/2000 | Doyle et al. |

FOREIGN PATENT DOCUMENTS

| EP | 0 849 358 A2 | 6/1998 |
| WO | WO 89/00600 | 1/1989 |
| WO | WO 99/36785 | 7/1999 |

OTHER PUBLICATIONS van Os, et al., Analytical Chimica Acta, 335, 1996, 209–216.*
van Os, et al., Analytica Chima Acta, 305, 1995, 18–25.*
K. Kobayashi et al., "Isolation of Reductase for SoxR that Governs an Oxidative Response Regulon from *Escherichia coli*", FEBS Letters, vol. 451, No. 3, May 28, 1999, pp. 227–230.
N. Eisaki et al., "Pyruvate Phosphate Dikinase from Thermophilic Actinomyces Microbispora Rosea Subsp. Aerata: Purification, Characterization and Molecular Cloning of the Gene", Biochimica Et Biophysica Acta Protein Structure and Molecular Enzymology, vol. 1431, No. 2, May 18, 1999, pp. 363–373.

* cited by examiner

*Primary Examiner*—Michael V. Meller
(74) *Attorney, Agent, or Firm*—Oliff & Berridge, PLC

(57) ABSTRACT

A method for stabilizing an enzyme during freezing, wherein the enzyme is in a zwitterionic buffer solution. The zwitterionic buffer is able to maintain the activity of the enzyme during freezing and thawing.

8 Claims, No Drawings

STABILIZATION OF ENZYMES DURING FREEZING

FIELD OF THE INVENTION

This invention relates to the preparation of stable enzyme formulations. In particular, this invention relates to a method for stabilising an enzyme during freezing.

BACKGROUND TO THE INVENTION

The preferred form for the supply of diagnostic reagents is a liquid. Liquid reagents require no preparation by the user, and therefore there is less risk of error.

If the reagents are to be prepared in a liquid form, the maintenance of stability is a major concern as it will usually be necessary to store and transport the reagents.

Examples of reagents which are bought commercially in a liquid form are those that include the enzymes glucose oxidase and horse-radish peroxidase, required for the measurement of glucose using a calorimetric method known as the Trinder method (Barham and Trinder, Analyst, 1972; 97:142). It is necessary to stabilise both the glucose oxidase and peroxidase enzymes to ensure that the enzymes function over their shelf-life. Typically, these enzymes are formulated with phosphate or Tris (hydroxymethyl)aminomethane buffers to maintain the pH of the reagent during storage and during the reaction. One difficulty that has been encountered is that the liquid preparations are often frozen during transport or on storage, and in these circumstances the enzymes are inactivated.

It is therefore desirable to provide compositions which effectively stabilise the diagnostic reagents on storage, and which offer further protection if freezing occurs.

U.S. Pat. No. 6,071,706 discloses a composition comprising αGST enzyme and a zwitterionic buffer, which may be stored at −20° C. The purpose is to retain the immunoreactivity of αGST, and there is no mention of retaining enzymic activity. Horse-radish peroxidase is mentioned, but this is only in the context of an enzyme-labelled anti-αGST IgG, which is used in the immunoassay. Stabilisation of this enzyme in solution is carried out in phosphate-buffered saline.

U.S. Pat. No. 5,910,422 and U.S. Pat. No. 4,465,770 both describe the stabilisation of specific enzymes (α-amylase and urease, respectively) in solution using polysaccharides or long chain oligosaccharides, e.g. sorbitol. A zwitterionic buffer may be provided to aid stabilisation of the enzymes in solution.

Although, in general, there are various methods for the stabilisation of various enzymes in solution, there is still a requirement for a useful method for stabilising enzyme activity, particularly for diagnostic reagents, during and after freezing.

SUMMARY OF THE INVENTION

According to the present invention, a method for stabilising the activity of an enzyme during freezing comprises providing the enzyme in a zwitterionic buffer solution.

The zwitterionic buffer solution has the capacity to effectively stabilise the enzyme in the liquid state and also provide protection if the end solution is frozen, either accidentally or otherwise.

In a preferred embodiment, the enzyme is glucose oxidase or horse-radish peroxidase.

According to a second aspect of the invention, a frozen solution of an enzyme is in a zwitterionic buffer.

Without wishing to be bound by theory, the ability of a zwitterionic buffer to stabilise the activity of enzymes may be a consequence of the ability of the buffers to prevent significant shifts in pH during freezing. It is known that phosphate buffers can cause large pH shifts during freezing (Rose et al Arch. Biochem. Biophys., 1959; 81:319–329), and it is believed that this may cause the denaturation of the enzymes. Typically, in a buffer composition, water will freeze first and ice crystals will grow. As the temperature approaches the eutectic points of the salts that are present, the salts crystallise out. The less soluble salts in a buffer will crystallise out of solution first, and this can cause a drastic change in the pH before the frozen solid is formed. However, a zwitterionic buffer may prevent this shift in pH, and thereby impart stability to the enzyme.

DESCRIPTION OF THE INVENTION

The present invention relies on the use of zwitterionic buffers to prepare the liquid reagent formulations. Zwitterionic buffers are sometimes referred to as "Goods" buffers (Good et al, Biochemistry, 1966; 5:467) and are commercially available. The buffers are generally zwitterionic aliphatic amines, with the majority being either substituted glycines or taurines. The buffers are distinct from the phosphate buffers used in the prior art to stabilise glucose oxidase reagents.

Suitable buffers which may be used in the present invention include Mops (3-[N-Morpholino]propanesulphonic acid), Mopso (3-[N-Morpholino]-2-hydroxypropanesulphonic acid) and Hepes (N-[2-hydroxyethyl]piperazine-N'-[2-ethanesulphonic acid]). Each of these buffers is available from commercial sources. Alternative zwitterionic buffers will be apparent to the skilled person.

The preparation of the buffer with the enzyme will be apparent to the skilled person, and the buffer will typically be prepared at a concentration of 20–250 mmol/l. Preferably, the buffer solution will be prepared with a pH of 7.

Although the buffers will prevent inactivation of the enzymes on freezing, it is preferred that the solutions are stored at 4° C.

The buffers may be used to stabilise any enzyme against the effects of freezing. In a preferred embodiment, the enzyme is glucose oxidase or horse-radish peroxidase. The enzymes may be the only active molecule present in the buffer solution. For example, the solution will not contain triglycerides or cholesterol which are sometimes present in some diagnostic kits which require peroxidase. The solutions may also be free from polysaccharides or oligosaccharides, i.e. sugars.

The following Example illustrates the invention.

EXAMPLE

Four different formulations, containing either Mops, phosphate buffer or a combination of both were prepared according to the formulations described below. Glucose oxidase (EC 1.1.3.4) from *Aspergillus niger* and horse-radish peroxidase (EC 1.11.1.7) were used. The other components of each formulation were included to promote the colourimetric glucose reaction or to help stabilise the reagents.

Formulation A
50 mmol/l Mops buffer

20 KU/l glucose oxidase
1.6 KU/l Peroxidase
11.0 mmol/l Phenol
0.05% sodium azide
0.03% polyvinylpyrrolidine
0.77 mmol/L 4-amino antipyrine The pH is adjusted to 7.0 with sodium hydroxide and/or hydrochloric acid.

Formulation B
150 mmol/l Mops buffer
20 KU/l glucose oxidase
1.6 KU/l Peroxidase
11.0 mmol/l Phenol
0.05% sodium azide
0.03% polyvinylpyrrolidine
0.77 mmol/L 4-amino antipyrine The pH is adjusted to 7.0 with sodium hydroxide and/or hydrochloric acid.

Formulation C
50 mmol/l Mops buffer
19.5 mmol/l sodium dihydrogen phosphate
30.5 mmol/l disodium hydrogen orthophosphate
19.20 KU/l glucose oxidase
1.6 KU/l Peroxidase
11.0 mmol/l Phenol
0.04% sodium azide
0.03% polyvinylpyrrolidine
0.77 mmol/L 4-amino antipyrine The pH is adjusted to 7.0 with sodium hydroxide and/or hydrochloric acid.

Formulation D (Control without Mops Buffer)
39 mmol/l sodium dihydrogen phosphate
61 mmol/l disodium hydrogen orthophosphate
20 KU/l glucose oxidase
1.6 KU/l Peroxidase
11.0 mmol/l Phenol
0.04% sodium azide
0.03% polyvinylpyrrolidine
0.77 mmol/L 4-amino antipyrine The pH was adjusted to 7.0 with sodium hydroxide and/or hydrochloric acid.

All of the formulations were frozen at −20° C. for 2 weeks and the activity of each enzyme measured after thawing. Peroxidase activity was measured using the method of Theorell, Acta Chem. Scand., 1950; 4:22. Glucose oxidase activity was measured using the method of Bergmeyer et al, Methods of Enzymatic Analysis, 1974; 1: 457 (Academic Press).

The results were compared to those obtained with the same reagent stored at 4° C. for 2 weeks. The absorbance of the reagent was measured at 500 nm and a factor determined from the absorbance, obtained after reacting the reagent with a 100 mmol/l glucose standard.

The formulations were also subjected to conditions of freezing and elevated temperature to mimic the conditions that could result on shipping of the reagent.

The reagents were subjected to two sets of test conditions; storage at either −20° C. or +37° C. Each test cycle consisted of 3 days at either −20° C. or 37° C., followed by 3 days at the normal storage temperature of 4° C. The reagents were subjected to 3 cycles for each test condition.

After completion, the stability of each reagent was determined by assessing the linearity and the ability to obtain the correct value for a range of quality control materials.

All glucose and enzyme assays were performed using an automated analyser.

Results

1) Enzyme activity

The concentrations of both glucose oxidase and horseradish peroxidase were measured in all reagents after 2 weeks at −20° C. The results are shown in Table 1. Reagent D which did not contain Mops buffer had no detectable glucose oxidase activity present and a decreased level of peroxidase after freezing and thawing. The other 3 reagents containing either solely Mops buffer at 2 different concentrations or Mops and phosphate buffers combined retained their glucose oxidase and peroxidase activity after freezing and thawing.

TABLE 1

| Formulation | % Gluc enzyme recovery | | % Peroxidase enzyme recovery | |
|---|---|---|---|---|
| | +4° C. | −20° C. | +4° C. | −20° C. |
| D | 79 | 0 | 173 | 87 |
| C | 75 | 80 | 93 | 91 |
| B | 70 | 74 | 137 | 132 |
| A | 43 | 46 | 115 | 112 |

2) Linearity (Tables 2, 3 4)

All formulations when stored at +4° C. showed linearity to 22 mmol/l of glucose. All formulations containing Mops buffer maintained their linearity of 22 mmol/l after 3 cycles at −20° C. Formulation D, without Mops buffer, was inactivated after 3 cycles and the glucose concentration could not be determined. All formulations after 3 cycles at +37° C. maintained their linearity.

TABLE 2

| | (+4° C. Shipping Study Cycle 3) | | | | | | |
|---|---|---|---|---|---|---|---|
| % SERUM | CONTROL | C | % dev | B | % dev | A | % dev |
| 10 | 2.35 | 2.33 | −0.9% | 2.42 | 3.0% | 2.36 | 0.4% |
| 20 | 4.29 | 4.27 | −0.5% | 4.35 | 1.4% | 4.3 | 0.2% |
| 30 | 6.64 | 6.62 | −0.3% | 6.73 | 1.4% | 6.63 | −0.2% |
| 40 | 9.12 | 9.12 | 0.0% | 9.26 | 1.5% | 9.13 | 0.1% |
| 50 | 11.26 | 11.37 | 1.0% | 11.51 | 2.2% | 11.38 | 1.1% |
| 60 | 13.72 | 13.69 | −0.2% | 14.07 | 2.6% | 13.77 | 0.4% |
| 70 | 16.01 | 16.06 | 0.3% | 16.29 | 1.7% | 16.03 | 0.1% |
| 80 | 18.55 | 18.54 | −0.1% | 18.92 | 2.0% | 18.7 | 0.8% |
| 90 | 20.66 | 20.6 | −0.3% | 20.79 | 0.6% | 20.75 | 0.4% |
| 100 | 22.96 | 22.89 | −0.3% | 23.43 | 2.0% | 23.09 | 0.6% |

TABLE 3

(−30° C. Shipping Study Cycle 3)

| % SERUM | CONTROL | C | % dev | B | % dev | A | % dev |
|---|---|---|---|---|---|---|---|
| 10 | 2.35 | 2.31 | −1.7% | 2.43 | 3.4% | 2.41 | 2.6% |
| 20 | 4.29 | 4.22 | −1.6% | 4.34 | 1.2% | 4.33 | 0.9% |
| 30 | 6.64 | 6.6 | −0.6% | 6.77 | 2.0% | 6.69 | 0.8% |
| 40 | 9.12 | 9.06 | −0.7% | 9.19 | 0.8% | 9.24 | 1.3% |
| 50 | 11.26 | 11.34 | 0.7% | 11.55 | 2.6% | 11.44 | 1.6% |
| 60 | 13.72 | 13.59 | −0.9% | 13.95 | 1.7% | 13.82 | 0.7% |
| 70 | 16.01 | 16.07 | 0.4% | 16.34 | 2.1% | 16.11 | 0.6% |
| 80 | 18.55 | 18.51 | −0.2% | 18.94 | 2.1% | 18.7 | 0.8% |
| 90 | 20.66 | 20.63 | −0.1% | 20.83 | 0.8% | 20.85 | 0.9% |
| 100 | 22.96 | 22.89 | −0.3% | 23.33 | 1.6% | 23.2 | 1.0% |

TABLE 4

(+37° C. Shipping Study Cycle 3)

| % SERUM | CONT. +4° C. | C | % dev | B | % dev | A | % dev | CONT. +37° C. | % dev |
|---|---|---|---|---|---|---|---|---|---|
| 10 | 2.35 | 2.28 | −3.0% | 2.34 | −0.4% | 2.47 | 5.1% | 2.3 | −2.1% |
| 20 | 4.29 | 4.29 | 0.0% | 4.29 | 0.0% | 4.67 | 8.9% | 4.26 | −0.7% |
| 30 | 6.64 | 6.6 | −0.6% | 6.64 | 0.0% | 7.15 | 7.7% | 6.62 | −0.3% |
| 40 | 9.12 | 9.21 | 1.0% | 9.19 | 0.8% | 10.07 | 10.4% | 9.17 | 0.5% |
| 50 | 11.25 | 11.51 | 2.2% | 11.43 | 1.5% | 12.46 | 10.7% | 11.45 | 1.7% |
| 60 | 13.72 | 13.9 | 1.3% | 13.89 | 1.2% | 15.3 | 11.5% | 13.95 | 1.7% |
| 70 | 16.01 | 16.21 | 1.2% | 16.25 | 1.5% | 17.77 | 11.0% | 16.21 | 1.2% |
| 80 | 18.55 | 18.81 | 1.4% | 18.88 | 1.8% | 20.6 | 11.1% | 18.82 | 1.5% |
| 90 | 20.66 | 21.08 | 2.0% | 20.69 | 0.1% | 23.04 | 11.5% | 20.9 | 1.2% |
| 100 | 22.96 | 23.41 | 2.0% | 23.35 | 1.7% | 25.75 | 12.2% | 23.13 | 0.7% |

3) Recovery of glucose in quality control serum (Tables 5, 6 and 7)

The formulations were tested against control serum samples. In the Tables, Precie-Path and Precie-Norm are available from Roche Diagnostics, and the multisera samples are available from Randox Laboratories.

All formulations gave acceptable values when stored at +4° C. After 3 cycles at −20° C., all Mops containing formulations gave values within ranges and deviations of less than 3% from the control reagent stored at 4° C. After 3 cycles at 37° C., all formulations gave acceptable values for each control serum sample.

TABLE 5

(+4° C. stability)

| SERUM | CONTROL | C | B | A | Target | Ranges |
|---|---|---|---|---|---|---|
| Precie-Path | 14.86 | 14.68 | 14.86 | 14.55 | 14.5 | 12.3 . . . 16.7 |
| Precie-Path | 5.87 | 5.85 | 5.95 | 5.86 | 5.71 | 4.84 . . . 6.58 |
| Multisera 094 SL | 3.4 | 3.41 | 3.46 | 3.4 | 3.43 | 2.92 . . . 3.94 |
| Multisera 100 UN | 6.24 | 6.23 | 6.32 | 6.22 | 6.02 | 5.42 . . . 6.62 |
| Multisera 200 SN | 6.18 | 6.17 | 6.28 | 6.13 | 6.08 | 4.86 . . . 7.30 |
| Randox Calibrator | 5.77 | 5.79 | 5.85 | 5.75 | 5.55 | n/a |

TABLE 6

(−20° C. stability at 2 weeks)

| SERUM | CONTROL | C | B | A | Target | Ranges |
|---|---|---|---|---|---|---|
| Precie-Path | 14.86 | 14.59 | 14.94 | 14.71 | 14.5 | 12.3 . . . 16.7 |
| Precie-Path | 5.87 | 5.8 | 5.91 | 5.88 | 5.71 | 4.84 . . . 6.58 |
| Multisera 094 SL | 3.4 | 3.38 | 3.49 | 3.42 | 3.43 | 2.92 . . . 3.94 |
| Multisera 100 UN | 6.24 | 6.21 | 6.31 | 6.26 | 6.02 | 5.42 . . . 6.62 |
| Multisera 200 SN | 6.18 | 6.11 | 6.25 | 6.13 | 6.08 | 4.86 . . . 7.30 |

TABLE 6-continued (−20° C. stability at 2 weeks)

| SERUM | CONTROL | C | B | A | Target | Ranges |
|---|---|---|---|---|---|---|
| Randox Calibrator | 5.77 | 5.79 | 5.86 | 5.78 | 5.55 | n/a |

TABLE 7

(+37° C. stability at 2 weeks)

| SERUM | CONT. +4° C. | C | B | A | CONT. +37° C. | Target | Ranges |
|---|---|---|---|---|---|---|---|
| Precie-Path | 14.86 | 14.59 | 14.94 | 14.71 | 14.92 | 14.5 | 12.3 ... 16.7 |
| Precie-Path | 5.87 | 5.8 | 5.91 | 5.88 | 5.86 | 5.71 | 4.84 ... 6.58 |
| Multisera 094 SL | 3.4 | 3.38 | 3.49 | 3.42 | 3.42 | 3.43 | 2.92 ... 3.94 |
| Multisera 100 UN | 6.24 | 6.21 | 6.31 | 6.26 | 6.28 | 6.02 | 5.42 ... 6.62 |
| Multisera 200 SN | 6.18 | 6.11 | 6.25 | 6.13 | 6.21 | 6.08 | 4.86 ... 7.30 |
| Randox Calibrator | 5.77 | 5.79 | 5.86 | 5.78 | 5.75 | 5.55 | n/a |

In summary, the use of Mops buffer as a sole buffer, or in combination with phosphate buffer, maintains the function of the enzymes after freezing and thawing.

What is claimed is:

1. A method for stabilising the activity of an enzyme selected from the group consisting of glucose oxidase and horseradish peroxidase during storage, said method comprising storing the enzyme in a zwitterionic buffer solution wherein the enzyme is stored in said zwitterionic buffer solution for at least three days.

2. A method according to claim 1, wherein the zwitterionic buffer is MOPS, MOPSO or HEPES.

3. A method according to claim 1, wherein the buffer is present at a concentration of 20 to 250 mmol/l.

4. A method according to claim 1, wherein the pH of the solution is 7.

5. A method according to claim 1, wherein the solution is stored at 4° C.

6. A method according to claim 1, wherein the solution is in a frozen state.

7. A method according to claim 1, wherein the solution does not contain any other active agents.

8. A method according to claim 1, wherein the enzyme is stored in said zwitterionic buffer solution for at least two weeks.

* * * * *